(12) United States Patent
Evans et al.

(10) Patent No.: US 10,709,594 B2
(45) Date of Patent: Jul. 14, 2020

(54) UNDERGARMENT FOR USE WITH HIP SPICA CAST

(71) Applicant: BSN medical, Inc., Charlotte, NC (US)

(72) Inventors: John C. Evans, Nr Rochdale (GB); Koen Jozef Maria Jorissen, Hamburg (DE)

(73) Assignee: BSN medical, Inc., Charlotte, NC (US)

( * ) Notice: Subject to any disclaimer, the term of this patent is extended or adjusted under 35 U.S.C. 154(b) by 306 days.

(21) Appl. No.: 15/692,216

(22) Filed: Aug. 31, 2017

(65) Prior Publication Data

US 2017/0360591 A1    Dec. 21, 2017

Related U.S. Application Data

(63) Continuation of application No. 13/897,520, filed on May 20, 2013, now Pat. No. 9,770,358.

(51) Int. Cl.
*A61F 5/05* (2006.01)
*A61F 5/058* (2006.01)
*A61F 5/01* (2006.01)

(52) U.S. Cl.
CPC ........ *A61F 5/05841* (2013.01); *A61F 5/0193* (2013.01)

(58) Field of Classification Search
CPC ........... A41B 9/00; A41B 9/001; A41B 9/004; A41B 9/005; A41B 9/007; A41B 9/12; A41D 2400/00; A41D 2400/44; A41D 2400/70; A41D 2500/00; A41D 2500/10; A61F 13/00; A61F 13/49; A61F 13/496; A61F 13/4963

USPC ............ 2/69, 73, 78.1, 78.2, 400–402, 404, 2/406–408, 272, 466; 128/98.1; 602/3, 602/60–62, 67

See application file for complete search history.

(56) References Cited

U.S. PATENT DOCUMENTS

| | | | | |
|---|---|---|---|---|
| 4,800,872 A | * | 1/1989 | Buese | A61F 13/04 427/407.3 |
| 5,267,944 A | * | 12/1993 | Fraser | A61F 5/3784 128/845 |
| 5,380,260 A | | 1/1995 | Blott | |
| 2005/0043664 A1 | | 2/2005 | Reaux | |
| 2008/0082035 A1 | | 4/2008 | Evans | |

(Continued)

FOREIGN PATENT DOCUMENTS

| | | |
|---|---|---|
| JP | 2008545490 A | 12/2008 |
| JP | 2009513281 A | 4/2009 |

(Continued)

OTHER PUBLICATIONS

International Search Report and Written Opinion for PCT/US2013/041802 dated Jan. 20, 2014.

(Continued)

*Primary Examiner* — Tarla R Patel
(74) *Attorney, Agent, or Firm* — Shumaker, Loop & Kendrick, LLP

(57) ABSTRACT

An undergarment for use with a cast tape to form a hip spica cast, such as a pantaloon-type hip spica cast. The cast includes at least one layer of a 3D spacer synthetic padding material formed into a fabric of monofilament yarns and fabricated into an anatomically correct undergarment structure for being positioned around a torso and residing directly against the skin of a hip spica cast patient.

21 Claims, 5 Drawing Sheets

(56) References Cited

U.S. PATENT DOCUMENTS

2012/0123377 A1* 5/2012 Back ................ A61F 13/15699
604/385.01
2012/0220908 A1* 8/2012 Evans .................. A61F 13/041
602/6

FOREIGN PATENT DOCUMENTS

WO         93/10732 A1    6/1993
WO    2010131840 A2   11/2010

OTHER PUBLICATIONS

"Application Manual Hip Spica Cast", Delta-Dry The Solution that Fits Your Life, BSN medical, Jun. 2001, http://www.bsnmedical.com/fileadmin/z-countries/O-Global/PDF/delta_dry_hip.pdf.

Material Safety Data Sheet, dated Aug. 1995, pp. 2/8-4/8, Johnson & Johnson Professional, Inc. Raynham, MA, USA.

Delta-Dry The Solution that Fits Your life, Application Manual Hip Spica Cast, 2011, pp. 1-11, BSN medical, Inc., Charlotte, NC, USA.

Delta-Dry The Solution that Fits Your life, pp. 1-2, BSN medical, Inc., Charlotte, NC, USA.

* cited by examiner

UNDERGARMENT FOR USE WITH HIP SPICA CAST

TECHNICAL FIELD AND BACKGROUND OF THE INVENTION

This invention relates to an undergarment formed of orthopedic padding, for example, for use as an undercast padding of the type used to protect and cushion the skin of a patient from the relatively rigid material of a cast, such as those constructed of plaster of Paris or synthetic cast tape. Specifically, this invention relates to a hip spica cast intended primarily for infants and other pediatric patients. The cast is constructed of an undercast padding material characterized by having a very open water and air transmissive structure enclosed within a very open water and air transmissive cast tape.

A cast which includes the torso of the body and one or more limbs is called a spica cast. A hip spica includes the torso of the body and one or more legs. A hip spica which covers only one leg to the ankle or foot may be referred to as a single hip spica, while one which covers both legs is called a double hip spica. A one-and-a-half hip spica encases one leg to the ankle or foot and the other to just above the knee. The extent to which the hip spica covers the torso depends greatly on the injury and the surgeon; the spica may extend only to the navel, allowing mobility of the spine and the possibility of walking with the aid of crutches, or may extend to the rib cage or even to the armpits in some rare cases. Hip spicas are used for a number of conditions and injuries, such as congenital hip dislocation or dysplasia.

In some cases, a hip spica may only extend down one or more legs to above the knee. Such casts, called pantaloon casts, are used to immobilize an injured lumbar spine or pelvis, in which case the torso portion of the cast usually extends to or just below the armpits. The specific example discussed in this application is such a pantaloon cast, but the invention is not limited to this particular type of cast.

A traditional hip spica cast is constructed from a simple stockinette and padding material made from cotton or synthetic fibers, and offers poor or no water resistant capability. Cotton and some synthetic padding actually absorb and retain large quantities of water. A hip spica cast is typically worn for a period of 6-10 weeks. During this period of time, traditional casts having a water-absorbent stockinette can promote skin maceration and discomfort. This is a particular problem with infants and very small children who are incontinent and therefore are far more likely to soil the cast with urine and feces. To facilitate toileting or diaper changing and hygienic cleaning, an opening, referred to as the "perineal opening", is typically created in the cast at the groin. It is formed either during cast application or after cast application by cutting the hole with a cast saw. The opening must then be petalled or lined to keep this area of the cast clean and dry. However, this is difficult, particularly with infants and small children. In reality, within a relatively short period of time after traditional hip spica cast application, the area around the perineal opening becomes soiled with urine and feces and develops foul odors that must be tolerated or masked with various deodorizers for a month or more. Rashes, maceration, skin and systemic infections, open sores and other conditions may retard the treatment schedule and impose pain and discomfort on the infant or pediatric patient.

The present invention provides a more conformable, water-resistant product that permits the material to be formed into an anatomically-shaped and sized undergarment that can be donned onto the patient, and then enclosed by wrapping with a suitable water and air permeable synthetic cast tape to form the spica cast.

One of the problems with conventional cast padding as well as commercially available water resistant padding is that the padding collapses underneath a cast over the duration of 4-6 weeks as water and perspiration are absorbed into the structure. This reduction in thickness and resultant increase in density retards moisture transfer by both wicking and evaporation, and lessens the protection offered by the padding.

The hip spica cast according to the present invention accommodates bathing, showering and contact with water for cleansing while permitting surface moisture to be dried, and moisture on the interior of the hip spica cast to evaporate relatively quickly, leaving the patient dry and comfortable. For smaller patients, the patient can be held in proximity to, for example, a handheld spray nozzle and the cast sprayed with a gentle spray of warm, cleansing water. Urine is readily washed away, and feces are dissolved, diluted and allowed to drain away. The patient is left clean and odor-free. Excess surface water is easily blotted away with an absorbent cloth or paper towel, and water on the interior evaporates within about one hour. This process can be repeated as necessary during the entire treatment period. Moreover, because of the ability to cleanse the patient as described above, it may not be necessary to provide the perineal opening in some instances.

SUMMARY OF THE INVENTION

Therefore, it is an object of the invention to provide a hip spica cast formed from a water and air permeable padding material formed into a garment, and enclosed within a water and air permeable synthetic cast tape. It is another object of the invention to provide an orthopedic padding that is comfortable when worn under a synthetic cast.

It is another object of the invention to provide a hip spica cast in the form of a garment that is relatively thin but still providing sufficient cushioning and thus provides a low profile undercast layer when properly overlapped during application.

It is another object of the invention to provide a hip spica cast that is relatively open and therefore breathable.

It is another object of the invention to provide a hip spica cast that is resistant to collapse during extended use.

It is another object of the invention to provide a hip spica cast that promotes drainage of water from the cast when wetting occurs.

It is another object of the invention to provide a breathable hip spica cast that is comfortable when worn against the skin under a wrapping of synthetic cast tape.

These and other objects of the present invention are achieved by providing an undergarment for use with a cast tape to form a hip spica cast, and comprising at least one layer of a 3D spacer synthetic padding material formed into a fabric of monofilament yarns and fabricated into an anatomically correct undergarment structure for being positioned around a torso and residing directly against the skin of a hip spica cast patient.

According to another embodiment of the invention, the undergarment has a torso portion and at least one integrally-formed leg portion.

According to another embodiment of the invention, the undergarment has a torso portion including a top opening for being positioned on a torso portion of the patient and at least one integrally-formed leg portion terminating in a leg opening adapted to reside between the hip and knee of the patient.

According to another embodiment of the invention, the undergarment has a torso portion including a top opening for being positioned on a torso portion of the patient and at first and second leg portions terminating in respective leg openings adapted to reside between the hips and knees of the patient.

According to another embodiment of the invention, the undergarment has a torso portion including a top opening for being positioned on a torso portion of the patient and at first and second leg portions terminating in respective leg openings adapted to reside between the hips and knees of the patient, and wherein the undergarment is formed of first and second overlaid padding layers defining an anterior side of the undergarment and third and fourth overlaid padding layers defining a posterior side of the undergarment.

According to another embodiment of the invention, the first and second padding layers and the third and fourth padding layers are joined along left and right seam lines extending from a top opening to first and second leg openings at a lowermost terminus of the undergarment.

According to another embodiment of the invention, the monofilament yarns are thermoplastic and the seam lines are formed by ultrasonic energy or other suitable methods, such as by butt or overedge seaming, or with an adhesive, either in tape or atomized glue form.

According to another embodiment of the invention, the undergarment includes a perineal opening.

According to another embodiment of the invention, the undergarment is configured to form an undergarment for a pantaloon hip spica cast.

According to another embodiment of the invention, the cast tape is selected from the group consisting of a synthetic fiber or fiberglass/non-fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long enough to allow application of the cast tape while still flexible over the undergarment.

According to another embodiment of the invention, an undergarment for use with cast tape to form a hip spica cast is provided, and includes at least one layer of a 3D spacer synthetic padding material formed into a knitted fabric of monofilament yarns and fabricated into an anatomically appropriate undergarment structure for being positioned around a torso and residing directly against the skin of a hip spica cast patient, the fabric for the padding material formed with at least 50 courses per meter preferably 200-850 courses per meter, and the padding material weighs between 50-400 g/m$^2$ and has a nominal thickness when not compressed or under tension of approximately 1.5-3.5 mm.

According to another embodiment of the invention, the undergarment has a torso portion including a top opening for being positioned on a torso portion of the patient and at first and second leg portions terminating in respective leg openings adapted to reside between the hips and knees of the patient, and wherein the undergarment is formed of first and second overlaid padding layers defining an anterior side of the undergarment and third and fourth overlaid padding layers defining a posterior side of the undergarment.

According to another embodiment of the invention, the first and second padding layers and the third and fourth padding layers are joined along left and right seam lines extending from a top opening to first and second leg openings at a lowermost terminus of the undergarment.

According to another embodiment of the invention, a hip spica cast is provided and includes, an undergarment comprising at least one layer of a 3D spacer synthetic padding material formed into a fabric of monofilament yarns and fabricated into an anatomically correct undergarment structure for being positioned around a torso and residing directly against the skin of a hip spica cast patient, and a cast tape having a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long enough to allow application of the cast tape while still flexible over the undergarment. The cast tape is positioned circumferentially over the undergarment and around the torso of the patient.

BRIEF DESCRIPTION OF THE DRAWINGS

Some of the objects of the invention have been set forth above. Other objects and advantages of the invention will appear as the invention proceeds when taken in conjunction with the following drawings, in which.

DETAILED DESCRIPTION OF PREFERRED EMBODIMENT OF THE INVENTION AND BEST MODE

Figure 2:
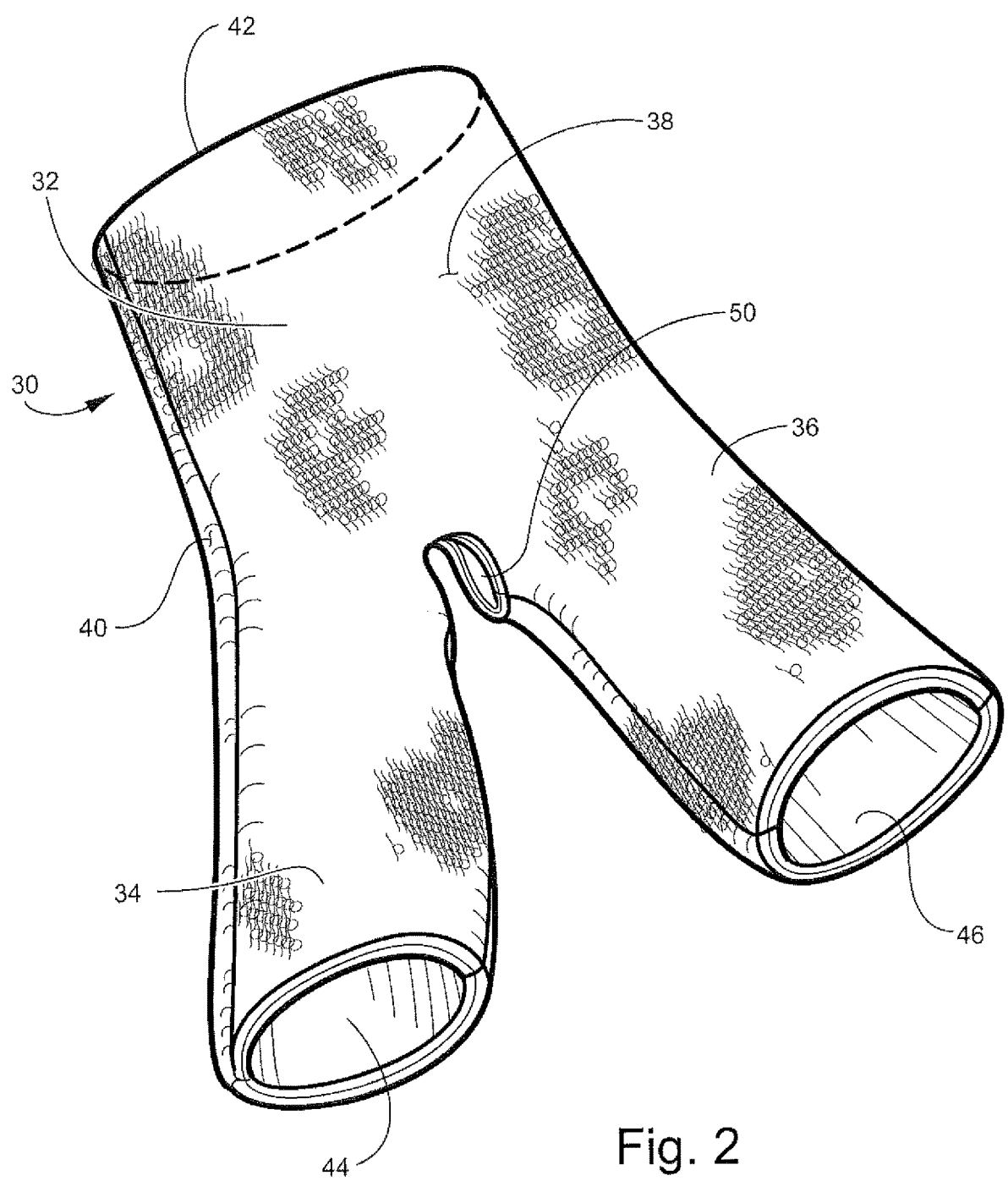
FIG. 2 is a perspective view of an alternative hip spica cast undergarment according to another embodiment of the invention, provided with a perineal opening.

Referring now specifically to the drawings, a hip spica undergarment 10 is shown. The particular hip spica undergarment 10 is a pantaloon hip spica that extends from below the armpits of the patient to above the knees. As noted above, there are other types of hip spica casts, and those are included within the scope of the invention even though not further described. The undergarment 10 includes a torso 12 and two integrally-formed legs 14 and 16 that are constructed of front and back blanks 18 and 20 of padding material. The patient is positioned in the undergarment 10 through a waist opening 22 with its legs extending through respective leg openings 24, 26. The undergarment 10 shown is seamed up the left and right sides and up the inside of each leg 14, 16 by ultrasonic welding of the synthetic material from which the blanks 18 and 20 are formed. One suitable material from which the undergarment 10 is constructed is a padding in sheet form that is presently sold in strips as Delta-Dry® brand synthetic padding manufactured and sold by BSN medical, Inc. and BSN medical, GmbH. FIG. 2 illustrates a hip spica pantaloon undergarment 30, which includes a torso 32 and two integrally-formed legs 34 and 36 that are constructed of front and back sheets of Delta-Dry® brand synthetic padding material 38 and 40. The patient is positioned in the undergarment 30 through a top opening 42 with its legs extending through respective leg openings 44, 46, The undergarment 30 shown is seamed up the left and right sides and up the inside of each leg 34, 36 by ultrasonic welding of the synthetic material from which the blanks 38 and 40 are formed. The seam may also be formed by any suitable method, such as by butt or overedge seaming, or with an adhesive, either in tape or atomized glue form. Undergarment 30 includes a perineal opening 50, which may be preformed in the undergarment 30 when constructed, or may be cut out to a desired size, position and shape during application.

Figure 1:
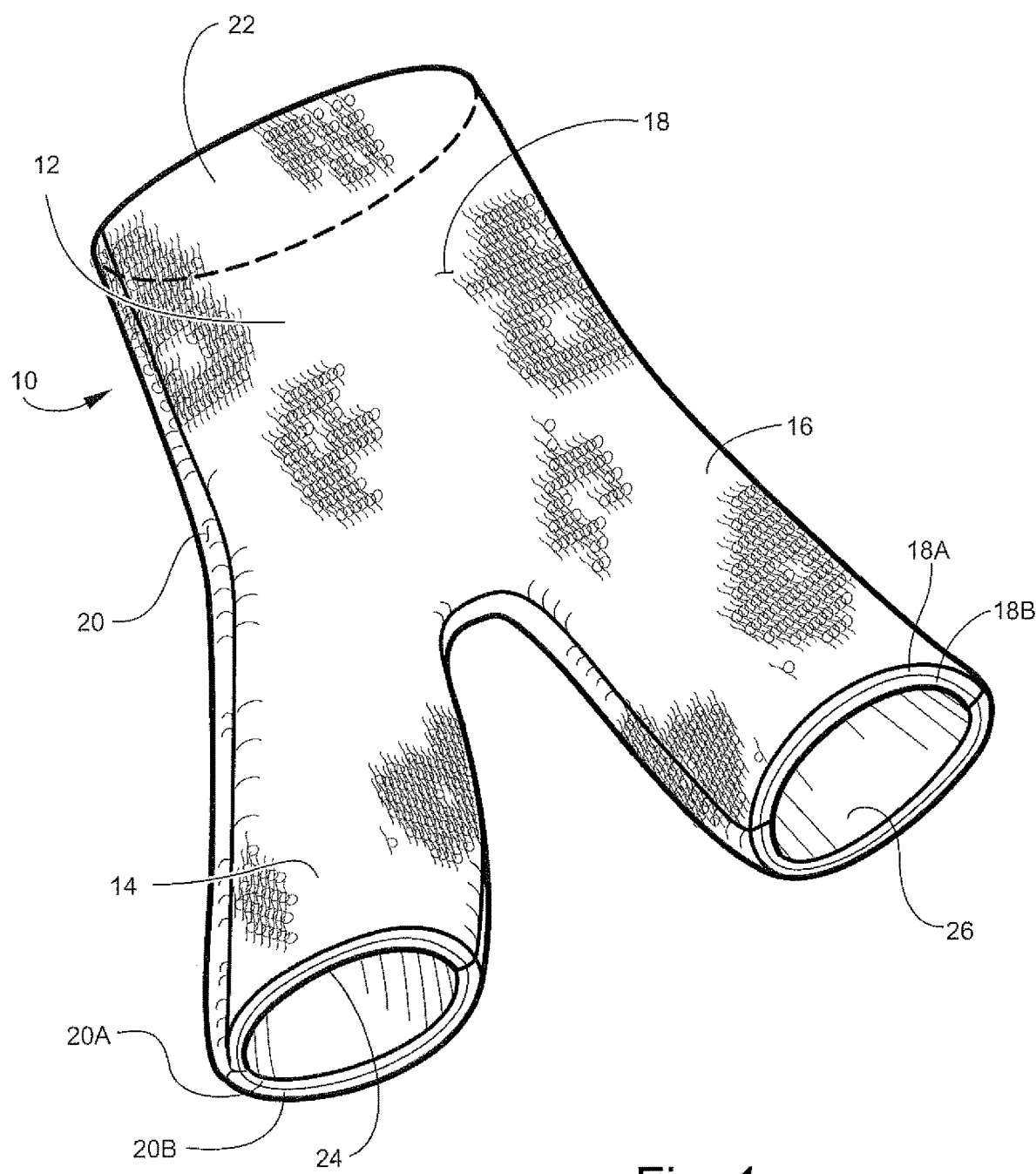
FIG. 1 is a perspective view of a hip spica cast undergarment according to one embodiment of the invention.
Figure 3:
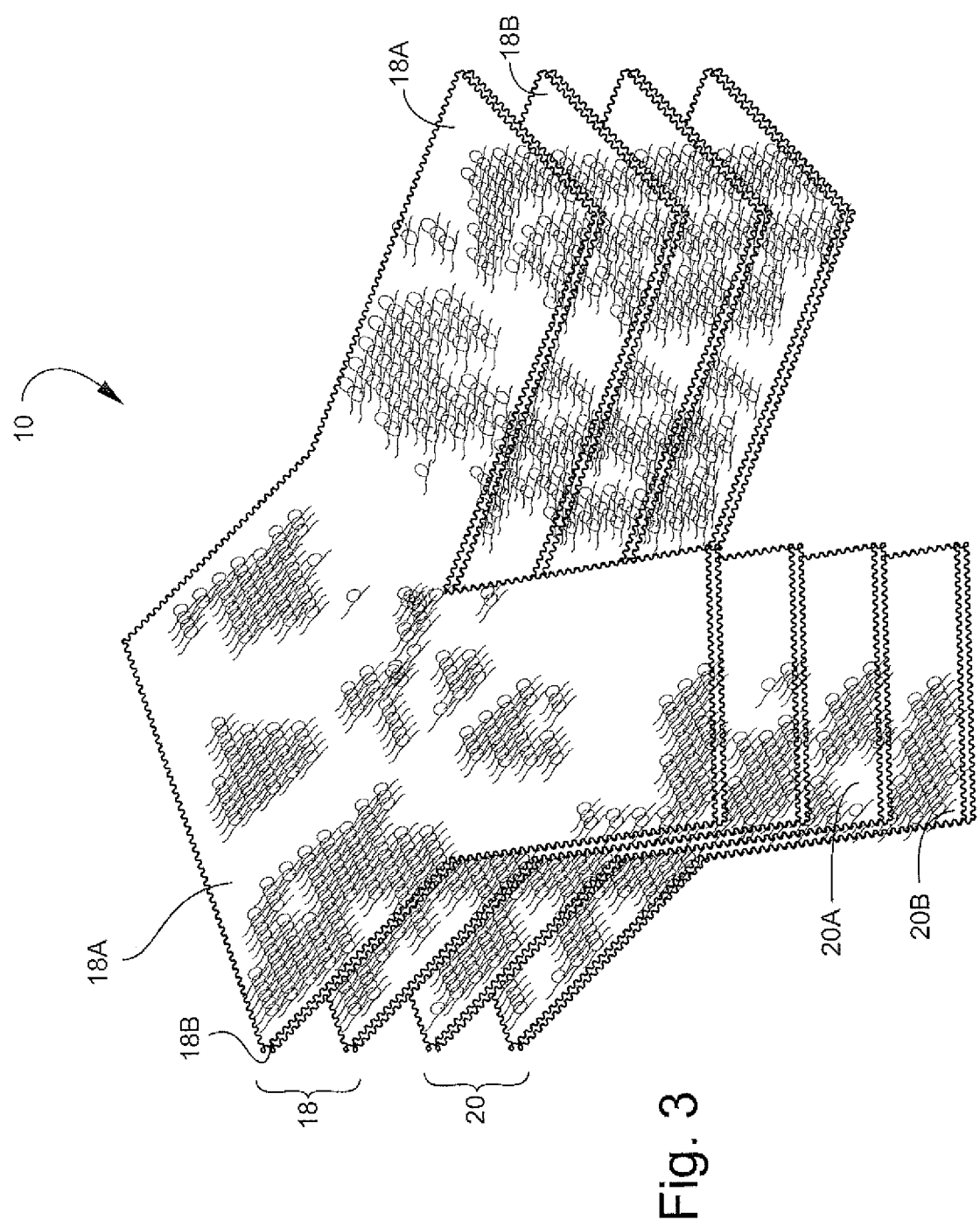
FIG. 3 is an exploded view showing formation of the undergarment of FIG. 1 or 2 by overlaying multiple sheets of padding material.

As shown in FIG. 3 with reference to the undergarment 10 shown in FIG. 1, each blank 18 and 20 are themselves preferably formed of two layers of padding material 18A, 18B, and 20A, 20B, such as Delta-Dry® brand synthetic padding. The double thickness provided by the layers 18A, 18B and 20A, 20B provide comfort and aids in protecting the skin from contact with the chemicals present on the cast tape applied over the undergarment 10. A double layer provides enhance comfort while still providing a moisture vapor transmission rate (MVTR) of over 1000 g/m²/24 hrs. Other embodiments may include single thickness or three or more thicknesses of the padding material.

The layers of padding shown in FIGS. 1, 2 and 3 can be constructed using any suitable hydrophobic/water resistant monofilament yarn such as polypropylene, polyester, polyethylene and nylon. The monofilament yarn used preferably has a diameter of at least 0.03 mm and is constructed with a 3D spacer fabric construction to provide sufficient cushioning and breathability, and it has been found that the use of a monofilament hydrophobic yarn on both faces and in the spacer area provides enhanced water resistance, light weight, breathability and resistance to collapse and degradation due to moisture and bacteria during extended use. Such a fabric is set out in US Published Application No. 2012/0220908, at paragraphs 0063-0068.

The padding material 18A, 18B, 20A, 20B can be constructed using any suitable organic or inorganic monofilament yarn, preferably a hydrophobic/water resistant monofilament yarn such as polypropylene, polyester, polyethylene and nylon. The monofilament yarn used for constructing the padding material preferably has a diameter of at least 0.03 mm. The padding material is constructed in a 3D spacer fabric construction to provide sufficient cushioning and breathability, and it has been found that the use of a monofilament hydrophobic yarn on both faces and in the spacer area provides enhanced water resistance, light weight, breathability and resistance to collapse and degradation due to moisture and bacteria during extended use.

The padding material is formed using any suitable fabric forming technology such as weaving, various knitting techniques such as, for example, weft knitting and warp knitting, non-woven, stitching, or a combination of these techniques. Preferably, the structure should provide some stretch in both the length-wise and width-wise directions, and facilitate conforming the undergarment 10 and 30 around an anatomical shape during application.

The padding material can be treated with one or more finishes to provide additional water resistance, anti-bacterial and/or anti-odor characteristics, or aromatherapy to improve the functionality or enhance the cast-wearing experience for the patient. Alternatively, the padding material can be fabricated from modified/treated monofilament yarns incorporating suitable fillers or finishes to improve the performance.

In one preferred embodiment, the undergarment 10 is constructed as a 3D spacer fabric using polypropylene monofilament and a low tack, pressure sensitive adhesive on one surface. The monofilament yarn has a diameter of at least 0.03 mm, and preferably between 0.05-0.25 mm. Preferably, the padding material requires no additional finish or water repellency treatment.

More specifically, one preferred embodiment of the padding material is constructed of a polypropylene monofilament yarn on a double needle bed knitting machine, and can be knitted on either a warp knitting Raschel machine or a Crochet knitting machine. The padding material is preferably constructed using a pillar and inlay stitch on the surfaces and a 3 or 5 needle V in the spacer area. The yarn has a diameter of 0.03-0.25 mm. The fabric for the padding material is formed with at least 50 courses per meter preferably 200-850 courses per meter. The padding material weighs between 50-400 g/m², and more preferably between 100-250 g/m². The padding material has a nominal thickness when not compressed or under tension of approximately 1.5-3.5 mm.

Alternatively, an undercast liner may be constructed as a spacer fabric with at least one of the yarns being a multifilament or spun yarn in order to provide even more patient comfort. The liner may be treated with suitable fluorochemical, silicone or other water repellant finish to improve drainage and provide faster drying.

The padding material may also be formed using any suitable fabric forming technology such as weaving, various knitting techniques such as, for example, weft knitting and warp knitting, non-woven, stitching, or a combination of these techniques. Preferably, the structure should provide some stretch in both the length-wise and width-wise directions, and facilitate conforming the undergarment 10 or 30 around the anatomical shape of the body torso and legs during application.

Figure 4:
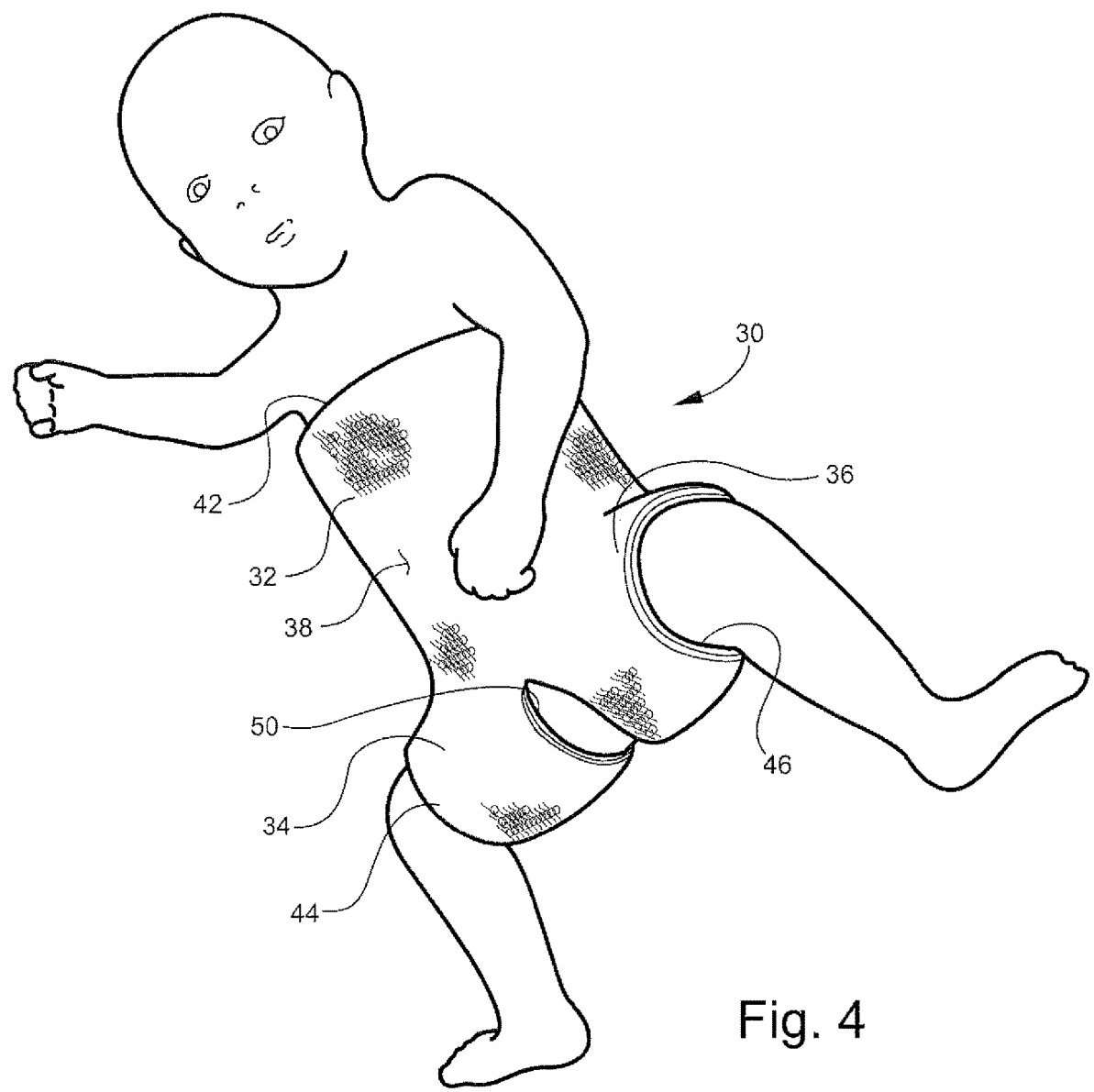
FIG. 4 is an environmental view showing a padding undergarment in place on an infant.
Figure 5:
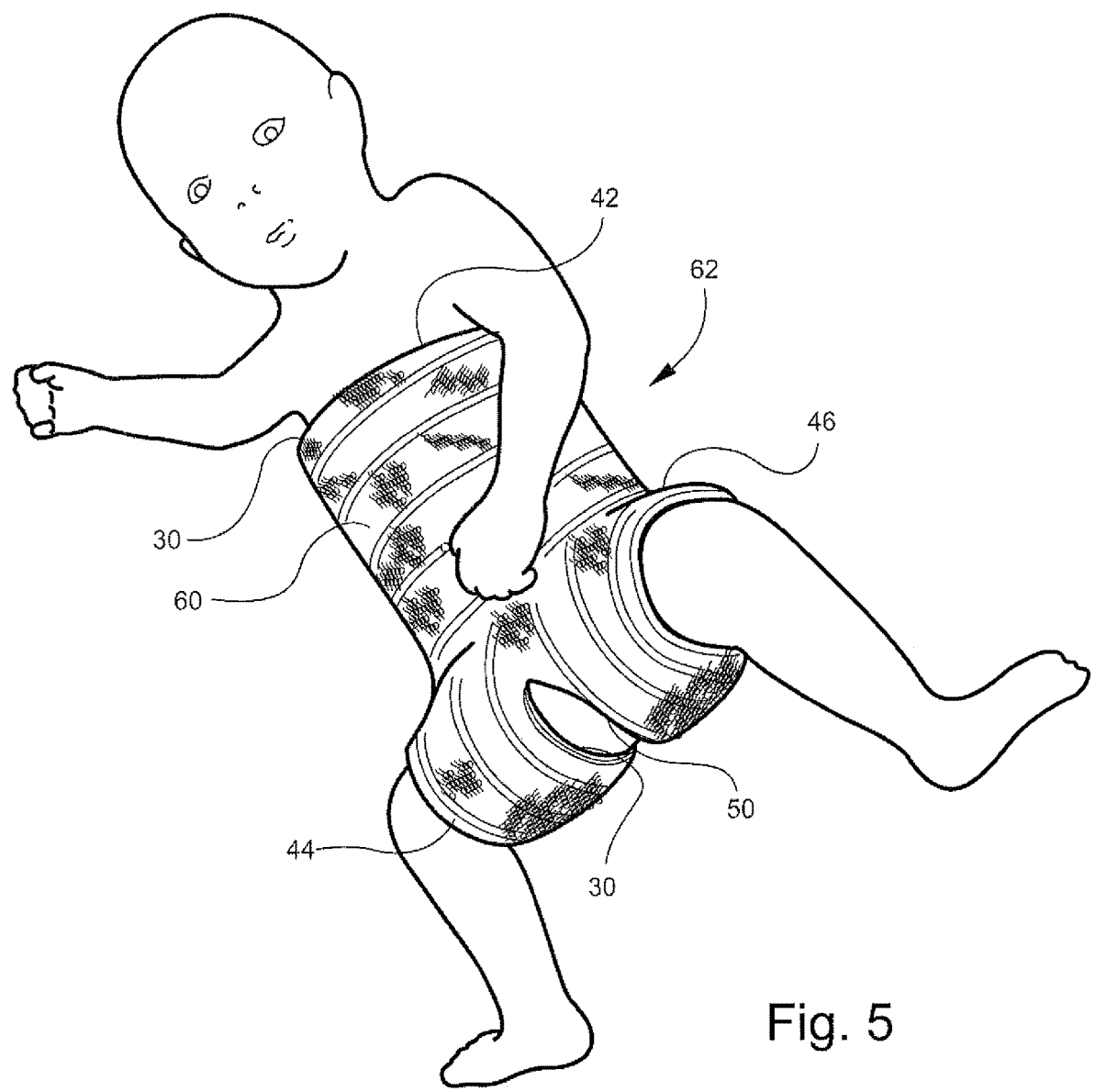
FIG. 5 is a view showing the hip spica cast after cast tape has been applied over the undergarment padding material.

As noted above, Delta-Dry® brand synthetic padding is preferred. The fabric weight off of the machine and after a 60 minute relaxation period is 105 g/m². Referring now to FIGS. 4 and 5, and by way of example, the undergarment 30 of FIG. 3 is applied to the infant by donning it over the legs and up across the torso to the medically-appropriate position-generally at or just below the armpits. As noted above, the stretch provided by the undergarment 30 permits a fast, accurate, closely-conforming application without wrinkles or creases. No stockinette or other material is used underneath the undergarment 30. It resides directly against the skin. The perineal opening 50 is either preformed in the undergarment 30 or formed during application.

As is shown in FIG. 5, after application of the undergarment 30, a wrapping of synthetic cast tape 60 is applied. The preferred cast tape is Delta-Cast® brand synthetic fiber cast tape or Delta-Lite® brand fiberglass cast tape manufactured and sold by BSN medical, Inc. and BSN medical, GmbH. These cast tapes are supplied in various widths, the particular width being a choice left to the physician or cast technician. Two-inch or three-inch cast tape is the most often used. The cast tape 60 is removed from its moisture impervious pouch, wetted, and excess water removed by wringing the cast tape 60 while wrapped in an absorbent towel. The cast tape 60 is then applied over the undergarment 30 by wrapping the cast tape 60 circumferentially around the patient and applied to the injured limb, taking care in the usual manner to properly overlap adjacent wraps, eliminate wrinkles and puckers and leaving a short width of exposed undergarment at the top opening 42, leg openings 44 and 46, and perineal opening 50. The result is the cast 62 shown in FIG. 5. The specific manner of application of the cast tape is a matter of medical procedure. One such procedure, illustrated with a prior art application of an underwrapping of strips of padding material, is contained in Application Manual-Hip Spica Cast, published by BSN medical, Inc., ©BSN medical, Inc., 2011, at pages 10-16.

The cast tape 60 hardens in several minutes to form a rigid cast 60 as shown in FIG. 5 that is nevertheless very water and air permeable. Typically, the torso portion of the cast 60 can be covered in a soft cloth or garment, or the patient's arms covered in a soft garment, in order to prevent chafing of the patient's arms against the outer surface of the cast tape 60 on the torso portion of the cast 62.

For infant or small juvenile patients, the patient can be held in proximity to, for example, a handheld spray nozzle and the cast sprayed with a gentle spray of warm, cleansing water. Urine is readily washed away, and feces are dissolved, diluted and allowed to drain away. The patient is left clean and odor-free, Excess surface water is easily blotted away with an absorbent cloth or paper towel, and water on the interior evaporates within about one hour. This process can be repeated as necessary during the entire treatment period. Moreover, because of the ability to cleanse the patient as described above, it may not be necessary to provide the perineal opening in some instances.

An undergarment for use in forming a hip spica cast, and a hip spica cast according to the invention have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

We claim:

1. A water and air permeable undergarment for a hip spica cast, comprising:
    (a) at least one layer of a 3D spacer synthetic padding material formed into a fabric of monofilament yarns and fabricated into an anatomically correct undergarment structure for being positioned around a torso of a patient and adapted to reside directly against skin of the patient;
    (b) the undergarment including a torso portion having a top opening for being positioned on the torso of the patient and having first and second leg portions terminating in respective leg openings adapted to reside between hips and knees of the patient; and
    (c) first and second overlaid padding layers defining an anterior side of the undergarment and third and fourth overlaid padding layers defining a posterior side of the undergarment.

2. The water and air permeable undergarment for a hip spica cast according to claim 1, and including a length of cast tape adapted to be wrapped circumferentially around the torso portion and the first and second leg portions.

3. The water and air permeable undergarment for a hip spica cast according to claim 1, wherein the first and second padding layers and the third and fourth padding layers are joined along left and right seam lines extending from a top opening to first and second leg openings at a lowermost terminus of the undergarment.

4. The water and air permeable undergarment for a hip spica cast according to claim 3, wherein the first, second, third, and fourth padding layers include thermoplastic monofilament yarns and the seam lines are formed by a seaming process selected from the group consisting of ultrasonic energy, butt seaming, overedge seaming, joining with an adhesive tape and joining in with an atomized glue.

5. The water and air permeable undergarment for a hip spica cast according to claim 1, wherein the undergarment includes a perineal opening.

6. The water and air permeable undergarment for a hip spica cast according to claim 1, wherein the undergarment is adapted for use with an overlying layer of cast tape as a pantaloon hip spica cast.

7. The water and air permeable undergarment for a hip spica cast according to claim 1, wherein the cast tape is selected from the group consisting of a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long to allow application of the cast tape while still flexible over the undergarment.

8. A water and air permeable undergarment for a hip spica cast, comprising:
    (a) at least one layer of a water and air permeable 3D spacer synthetic padding material formed into a knitted fabric of monofilament yarns and fabricated into an anatomically appropriate undergarment for being positioned around a torso of a patient and adapted to reside directly against skin of the patient;
    (b) the fabric of the padding material having 200-850 courses per meter;
    (c) the padding material weighing between 50-400 $g/m.^2$ and having a nominal thickness when not compressed or under tension of approximately 1.5-3.5 mm; and
    (d) a wrapping of cast tape overlying the undergarment.

9. The water and air permeable undergarment for a hip spica cast according to claim 8, wherein the undergarment has a torso portion including a top opening for being positioned on a torso portion of the patient and at first and second leg portions terminate in respective leg openings adapted to reside between hips and knees of the patient, and wherein the undergarment is formed of first and second overlaid padding layers defining an anterior side of the undergarment and third and fourth overlaid padding layers defining a posterior side of the undergarment.

10. The water and air permeable undergarment for a hip spica cast according to claim 9, wherein the first and second padding layers and the third and fourth padding layers are joined along left and right seam lines extending from a top opening to first and second leg openings at a lowermost terminus of the undergarment.

11. The water and air permeable undergarment for a hip spica cast according to claim 8, wherein the padding material weighs between 100-250 $g/m.^2$.

12. A water and air permeable undergarment for a hip spica cast, comprising:
    (a) a water and air permeable 3D spacer synthetic padding material formed into a fabric of monofilament yarns and fabricated into an anatomically correct undergarment structure for being positioned around a torso of a patient and adapted to reside directly against skin of the patient; and
    (b) a cast tape selected from the group consisting of a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long to allow application of the cast tape while still flexible over the undergarment and adapted to be positioned circumferentially over the undergarment and around the torso of the patient.

13. The water and air permeable undergarment for a hip spica cast according to claim 12, wherein the undergarment comprises a pantaloon garment having a torso portion and first and second leg portions.

14. The water and air permeable undergarment for a hip spica cast according to claim 12, wherein the undergarment includes first and second padding layers and the third and fourth padding layers joined along left and right seam lines extending from a top opening to first and second leg openings at a lowermost terminus of the undergarment.

15. The water and air permeable undergarment for a hip spica cast according to claim 12, wherein the padding material weighs between 100-250 g/m.$^2$.

16. The water and air permeable undergarment for a hip spica cast according to claim 12, wherein the monofilament yarns are thermoplastic and the seam lines are formed by a seaming process selected from the group consisting of ultrasonic energy, butt seaming, overedge seaming, joining with an adhesive tape and joining in with an atomized glue.

17. The water and air permeable undergarment for a hip spica cast according to claim 13, wherein the undergarment includes a perineal opening.

18. A water and air permeable undergarment for a hip spica cast, comprising:
 (a) a pantaloon undergarment having a torso portion and first and second leg portions formed of a water and air permeable 3D spacer synthetic padding material formed into a fabric of monofilament yarns and fabricated into an anatomically correct undergarment structure for being positioned around a torso of a patient and adapted to reside directly against skin of the patient;
 (b) the pantaloon undergarment including first and second padding layers and third and fourth padding layers joined along left and right seam lines extending from a top opening to first and second leg openings at a lowermost terminus of the undergarment;
 (b) a cast tape adapted to be positioned circumferentially over the pantaloon undergarment and around the torso of the patient and selected from the group consisting of a synthetic fiber or fiberglass/non fiberglass substrate coated or saturated with a moisture-curable resin and stored in a flexible condition in a moisture impervious package until use, at which time removal of the cast tape from the moisture impervious package and exposure to moisture causes the substrate to harden over a time period sufficiently long to allow application of the cast tape while still flexible over the undergarment.

19. The water and air permeable undergarment for a hip spica cast according to claim 18, wherein the padding material weighs between 100-250 g/m.$^2$.

20. The water and air permeable undergarment for a hip spica cast according to claim 18, wherein the monofilament yarns are thermoplastic and the seam lines are formed by a seaming process selected from the group consisting of ultrasonic energy, butt seaming, overedge seaming, joining with an adhesive tape and joining in with an atomized glue.

21. The water and air permeable undergarment for a hip spica cast according to claim 18, wherein the undergarment includes a perineal opening.

* * * * *